US008821434B2

(12) United States Patent
Hunter et al.

(10) Patent No.: US 8,821,434 B2
(45) Date of Patent: Sep. 2, 2014

(54) DELIVERY OF A SOLID BODY AND/OR A FLUID USING A LINEAR LORENTZ-FORCE ACTUATED NEEDLE-FREE JET INJECTION SYSTEM

(75) Inventors: Ian W. Hunter, Lincoln, MA (US); Andrew J. Taberner, Auckland (NZ); N. Catherine Hogan, Boston, MA (US)

(73) Assignee: Massachusetts Institute Of Technology, Cambridge, MA (US)

( * ) Notice: Subject to any disclaimer, the term of this patent is extended or adjusted under 35 U.S.C. 154(b) by 140 days.

(21) Appl. No.: 13/269,322

(22) Filed: Oct. 7, 2011

(65) Prior Publication Data

US 2012/0095435 A1 Apr. 19, 2012

Related U.S. Application Data (60) Provisional application No. 61/391,053, filed on Oct. 7, 2010, provisional application No. 61/405,355, filed on Oct. 21, 2010.

(51) Int. Cl.
*A61M 5/30* (2006.01)

(52) U.S. Cl.
USPC ............... 604/70; 604/59; 604/68; 604/72

(58) Field of Classification Search
CPC . A61M 5/30; A61M 5/2053; A61M 37/0069; A61M 2005/3104; A61M 2210/0612; A61F 9/0017; A61F 9/0008
USPC .......................... 604/57–64, 68–72
See application file for complete search history.

(56) References Cited

U.S. PATENT DOCUMENTS 5,865,795 A * 2/1999 Schiff et al. .................... 604/70
5,879,327 A * 3/1999 Moreau DeFarges et al. .. 604/68
(Continued)

FOREIGN PATENT DOCUMENTS

WO WO-03/035149 A1 5/2003
WO WO-03/037403 A1 5/2003
(Continued)

OTHER PUBLICATIONS

International Preliminary Report on Patentability of International mailed on Apr. 18, 2013, in Application No. PCT/US2011/055443, "Delivery of a Solid Body and/or a Fluid Using a Linear Lorentz-Force Actuated Needle-Free Jet Injection System."

(Continued)

*Primary Examiner* — Emily Schmidt
(74) *Attorney, Agent, or Firm* — Hamilton, Brook, Smith & Reynolds, P.C.

(57) ABSTRACT

A method for transferring a solid body across a surface of a biological body includes (i) applying an electrical input to a controllable electromagnetic actuator; (ii) producing with the electromagnetic actuator a mechanical force corresponding to the electrical input; and (iii) applying the mechanical force to a reservoir coupled at one end to a nozzle, the mechanical force producing a pressure within the reservoir, a magnitude of the pressure varying with the mechanical force and causing ejection of a fluid from the reservoir to drive the solid body into the biological body. A method for delivering a substance to a target body includes (i) positioning a needle-free injector proximate to a surface of the target body; (ii) injecting the substance into the target body; and (iii) while injecting, moving the needle-free injector along the surface, thereby sweeping the surface.

22 Claims, 10 Drawing Sheets

(56) References Cited

U.S. PATENT DOCUMENTS

| | | | |
|---|---|---|---|
| 6,258,062 B1* | 7/2001 | Thielen et al. | 604/141 |
| 6,939,323 B2 | 9/2005 | Angel et al. | |
| 7,066,922 B2 | 6/2006 | Angel et al. | |
| 7,364,568 B2 | 4/2008 | Angel et al. | |
| 7,425,204 B2 | 9/2008 | Angel et al. | |
| 7,429,258 B2 | 9/2008 | Angel et al. | |
| 7,530,975 B2 | 5/2009 | Hunter | |
| 7,645,263 B2 | 1/2010 | Angel et al. | |
| 7,651,475 B2 | 1/2010 | Angel et al. | |
| 7,833,189 B2 | 11/2010 | Hunter et al. | |
| 8,105,270 B2 | 1/2012 | Hunter | |
| 8,172,790 B2 | 5/2012 | Hunter et al. | |
| 8,328,755 B2 | 12/2012 | Hunter et al. | |
| 2003/0083618 A1 | 5/2003 | Angel et al. | |
| 2004/0106894 A1* | 6/2004 | Hunter et al. | 604/66 |
| 2004/0260234 A1* | 12/2004 | Srinivasan et al. | 604/66 |
| 2006/0258986 A1 | 11/2006 | Hunter et al. | |
| 2007/0055200 A1* | 3/2007 | Gilbert | 604/70 |
| 2007/0129693 A1 | 6/2007 | Hunter et al. | |
| 2008/0009788 A1 | 1/2008 | Hunter et al. | |
| 2008/0033351 A1* | 2/2008 | Trogden et al. | 604/57 |
| 2008/0274979 A1* | 11/2008 | Ellis-Behnke et al. | 514/14 |
| 2008/0281273 A1 | 11/2008 | Angel et al. | |
| 2009/0240230 A1 | 9/2009 | Azar et al. | |
| 2010/0004624 A1 | 1/2010 | Hunter | |
| 2010/0016827 A1 | 1/2010 | Hunter et al. | |
| 2011/0054354 A1 | 3/2011 | Hunter et al. | |
| 2011/0054355 A1 | 3/2011 | Hunter et al. | |
| 2011/0071505 A1* | 3/2011 | Rickard et al. | 604/540 |
| 2011/0082388 A1 | 4/2011 | Hunter et al. | |
| 2011/0143310 A1 | 6/2011 | Hunter | |
| 2011/0166549 A1 | 7/2011 | Hunter et al. | |
| 2011/0257626 A1 | 10/2011 | Hunter et al. | |
| 2011/0311939 A1 | 12/2011 | Hunter | |
| 2012/0003601 A1 | 1/2012 | Hunter et al. | |
| 2012/0089114 A1 | 4/2012 | Hemond et al. | |

FOREIGN PATENT DOCUMENTS

| | | | |
|---|---|---|---|
| WO | WO-03/037404 A1 | 5/2003 | |
| WO | WO-03/037405 A1 | 5/2003 | |
| WO | WO-03/037406 A2 | 5/2003 | |
| WO | WO-03/037407 A1 | 5/2003 | |
| WO | WO-03/039635 A2 | 5/2003 | |
| WO | WO-2004/021882 A2 | 3/2004 | |
| WO | WO-2004/022138 A2 | 3/2004 | |
| WO | WO-2006/086719 A1 | 8/2006 | |
| WO | WO-2006/086720 A2 | 8/2006 | |
| WO | WO-2006/086774 A2 | 8/2006 | |
| WO | WO-2007/058966 A1 | 5/2007 | |
| WO | WO-2008/027579 A1 | 3/2008 | |
| WO | WO-2011/028716 A1 | 3/2011 | |
| WO | WO-2011/028719 A2 | 3/2011 | |
| WO | WO-2011/075535 A1 | 6/2011 | |
| WO | WO-2011/075545 A1 | 6/2011 | |
| WO | WO-2011/084511 A1 | 7/2011 | |
| WO | WO 2012/048268 A2 | 4/2012 | |
| WO | WO 2012/048277 A2 | 4/2012 | |

OTHER PUBLICATIONS

International Search Report and Written Opinion mailed Jul. 4, 2012 in International Patent Application No. PCT/US2011/055454.

Hemond, Brian D., et al., "A Lorentz-Force Actuated Autoloading Neddle-free Injector," Proceedings of the 28th IEEE, EMBS Annual International Conference, Aug. 30-Sep. 3, 2006, pp. 679-682.

Hemond, Brian D., et al., "Development and Performance of a Controllable Autoloading Neddle-Free Jet Injector," Journal of Medical Devices, Mar. 2011, vol. 5, pp. 015001-1 through 015001-7.

Stachowiak, Jeanne C., et al., "Dynamic control of needle-free jet injection," Journal of Controlled Release, Release 135 (2009), pp. 104-112.

Taberner, Andrew J., et al., "A Portable Neddle-free Jet Injector Based on a Custom High Power-density Voice-coil Actuator," Proceedings of the 28th IEEE, EMBS Annual International Conference, Aug. 30-Sep. 3, 2006, pp. 5001-5004.

Chen, K., et al., "A Needle-free Liquid Injection System Powered by Lorentz-force Actuator," *2010 International Conference on Mechanic Automation and Control Engineering (MACE2010)*, (Jun. 26-28, 2010).

Chen, K., and Zhou, H., "An experimental study and model validation of pressure in liquid needle-free injection," *Int'l J. Phy. Sci.*, 6(7):1552-1562 (Apr. 4, 2011).

Declaration of Non-Establishment of International Search Report, with Written Opinion of the International Searching Authority in International Application No. PCT/US2011/055443, 7 pages, mailed Feb. 15, 2012.

Invitation to Pay Additional Fees and, Where Applicable, Protest Fees mailed Feb. 28, 2012 in International Patent Application No. PCT/US2011/055454.

Taberner, et al., "Needle-free jet injection using real-time controlled linear Lorentz-force actuators," *Med. Eng. Phys.*, (2012) doi: 10.1016/j.medengphy.2011.12.010.

International Preliminary Report on Patentability mailed on Apr. 18, 2013, in Application No. PCT/US2011/055454, "Injection Methods Using a Servo-Controlled Needle-Free Injector."

* cited by examiner

DELIVERY OF A SOLID BODY AND/OR A FLUID USING A LINEAR LORENTZ-FORCE ACTUATED NEEDLE-FREE JET INJECTION SYSTEM

RELATED APPLICATIONS

This application claims the benefit of and priority to U.S. provisional patent application Ser. No. 61/391,053, filed Oct. 7, 2010 and U.S. provisional patent application Ser. No. 61/405,355, filed Oct. 21, 2010; the entireties of both applications are incorporated by reference herein.

FIELD OF INVENTION

This application relates generally to needle-free transdermal transport devices, particularly to methods of delivering substances, including solid bodies by using needle-free devices.

BACKGROUND

Needle-free jet injection provides an equally effective alternate route for the administration of drugs that is free of many of the problems associated with conventional delivery using a needle and syringe (e.g., needle stick injections, expense associated with disposal of sharps, belonephobia, and compliance). Jet injectors can be classified by the actuator used to generate the high pressures required for injection; ranging from 5.5 MPa to ~30 MPa dependent on the size of the orifice, the desired depth of injection, the viscosity of the drug, and individual skin variation.

A continuing issue with drug delivery using needle-free jet injectors is repeatable delivery of a specific amount of active drug to the target tissue. Commercial devices powered by springs or compressed gases have little to no control over the pressure applied to the drug during the time course of the injection, potentially resulting in shearing and loss of activity of larger therapeutic protein molecules. Furthermore, these devices are often loud and sometimes deemed painful. While some pressure pulse shaping may be afforded by using variable gas orifices and fast/slow pyrotechnic charges, these techniques, while an improvement, may not provide precise control. More recently, Stachowiak et al. developed a jet injector that uses a dynamically controllable piezoelectric stack placed within a mechanical flexure. By decoupling the depth and dose functions of the jet injector, they have demonstrated that penetration depth in tissue model materials (i.e. acrylamide) may be precisely controlled by adjusting the proportion of the injection volume delivered at high speed. However, the piston stroke and hence the volume of fluid delivered may be limited by the design, which is difficult to scale.

An electrically driven linear Lorentz-force motor, affords robust and precise control over coil position and thereby over both the depth and volume of drug delivered without compromising stroke (e.g., 25 mm in current device) and therefore volume (e.g., 250 μL in current device). See B. Hemond, D. M. Wendell, N. C. Hogan, A. J. Taberner, and I. W. Hunter, "A Lorentz-force actuated autoloading needle-free injector," in: Proceedings of the 28th Annual International Conference of the Engineering Medicine and Biology Society 1 (2006) 679-682, http://ieeexplore.ieee.org/hemond, and A. J Taberner, N. B. Ball, N. C. Hogan, and I. W. Hunter, "A portable needle-free jet injector based on a custom high power-density voice-coil actuator," in: Proceedings of the 28th Annual International Conference of the Engineering Medicine and Biology Society 1 (2006) 5001-4, http://ieeexplore.ieee.org/taberner; both references are incorporated herein in their entireties.

Energy delivered to the actuator in an electrical form allows one to impose a time varying pressure (or velocity) profile (i.e., waveform) on the drug volume during the course of the injection through the use of a monitored and servo controlled amplifier. See Hemond et al. and Taberner et al., and also B. Hemond, A. Taberner, C. Hogan, B. Crane, and I. Hunter, "Development and performance of a controllable autoloading needle-free jet injector," *J Med Devices* 5 (2010) 015001-1-015001-7, both references are incorporated by reference herein in their entireties.

Controlling the volume of drug delivered ensures that the relevant dose is delivered (e.g., insulin), potentially reduces the dose (e.g., ID delivery of vaccines normally administered intramuscularly [IM] or subcutaneously [SC]) and cost for each deliverable, and increases the availability of drugs in limited supply (e.g., vaccines). Controlling the depth of injection ensures delivery to the appropriate tissue layer regardless of body type and enables more accurate delivery of certain drugs that are most effective when delivered SC (e.g., insulin) or IM (e.g., tetanus) or when delivered ID at normal or reduced volume (e.g., lidocaine, TB, rabies, HBV, influenza, etc.).

Typically, jet injectors are used to propel liquid (e.g., insulin, human growth hormone, etc.), reconstituted drug formulations (e.g., vaccines, MAbs), powdered drug, or drug coated particles (e.g., inert gold particles) into the target tissue. However, concomitant with the continual development of protein-based therapeutics and vaccines has been the development of new drug formulations to enhance delivery, stability, and efficacy (i.e., bioavailability) and a need for more innovative methods of delivery.

Environmentally responsive systems (e.g., hydrogels), liposomes, and biodegradable polymers, both bulk (e.g., polylactides, polyglycolides, and their copolymers) and surface erodible materials, have attempted to address this need by providing controlled release systems thereby greatly reducing the frequency of dosing. However, delivery often involves invasive implantation.

While several studies have reported using the PowderJect device, currently owned by PowderJect Vaccines, Inc., to assess epidermal powder immunization using gold coated particles (1.5 to 2.5 μm is size), vaccine formulations, etc., little work has been done on evaluating the use of jet injectors to deliver biodegradable polymeric/drug controlled release formulations. A spring-actuated device has been proposed for delivering a preferred biodegradable pioneer projectile and subsequent therapeutic, together referred to as an injectate to a human or animal. However, unlike the linear Lorentz-force actuated jet injector described herein, springs provide little to no control over the pressure vs. time profile, a requisite for delivery to specific target tissues/body locations in a heterogeneous population.

There is a need for improved targeting of drug to specific sites combined with the controlled release of drug from these delivered bodies, to thereby increase drug efficacy and reduce repeated dosing.

SUMMARY

Delivery of solid bodies, for example polymeric controlled release formulations, powdered vaccines, drug-coated materials etc., across a surface of a solid body using a servo-controlled linear Lorentz-force actuated jet injector, as described herein, may provide improved targeting of drug delivery to specific sites. Further, use of this platform technology for delivery of solids other than biologicals opens a range of possibilities that may include for example delivery of RFID tags for tracking and managing inventory, people, assets etc., delivery of self-assembling scaffolds to build for example circuit boards or cell scaffolds, delivery of metal or coated wires or polymers for use as electrodes, antennae, etc., delivery of sensors, and tattooing for cosmetic, medical, professional, and personal purposes.

In addition, the jet injector may be used to sweep a surface using one or more actuators, thereby allowing movement in multiple directions in one plane and delivery to different depths to create a multi-layered structure that may be a material part (e.g., bar codes etc.) or a structure that may be of potential use in imaging tissue (e.g., different layers within the tissue) and/or other materials.

Embodiments of the invention relate to use of a servo-controlled linear Lorentz-force jet injection technology to deliver one or more solid bodies to a target, for example skin. Delivery may involve using the device configuration as described in A. J. Taberner, N. C. Hogan, and I. W. Hunter, "Real-time feedback-controlled needle-free jet injection using linear Lorentz-force motors," manuscript submitted to *Medical Engineering & Physics* August 2011, and A. J. Taberner, N. B. Ball, N. C. Hogan, and I. W. Hunter, A portable needle-free jet injector based on a custom high power-density voice-coil actuator, in *Proceedings of the 28th Annual International Conference of the IEEE Engineering and Medicine and Biology Society*, Vol. 1-15 (2006) 2531-2534, both references are incorporated herein by reference in their entireties.

Delivery may also take place with a modified configuration in which the nozzle has been replaced with a disposable cartridge containing the solid body. Actuation of the coil motor may result in a plunger forcing fluid through either the nozzle orifice or capsule orifice, causing the solid body to be ejected with sufficient force to penetrate the target.

The methods described herein may provide a number of advantages and improvements over existing methods, including the following:

a. The ability to control the injection depth may allow for more accurate delivery of the solid body to the desired position within the target.
b. Packaging therapeutics in a solid form may improve stability and increase shelf life.
c. The ability to deliver solid particles may allow particles to be tailored for optimal pharmacokinetic effect (e.g., extended or immediate release formulations).
d. Delivery of solid particles may prove painless as delivery does not involve the large volumes often associated with delivery of liquids; pain being a function of extension/tearing of the tissue and not the drug itself.
e. The bidirectionality of the actuator allows the user to load particles in solution into the ampoule from a storage vial/container for just-in-time delivery
f. In the case of drug-filled capsules/implants, the drug may be slowly released from the capsule/implant, thereby reducing the requisite number of injections which should improve acceptance and compliance.
g. The implant can be pre-loaded into the sealed, sterile cartridge which can be stored at the appropriate temperature until use at which point it can be threaded onto the end of the sterile piston shaft for delivery. Because of the sterile seal on the end of the nozzle, retention of the implant is ensured until the device is fired regardless of the position of the jet injection (i.e., how the user is holding the device).
h. Minimal preparation steps may result in fewer errors etc. and less risk of contamination.
i. A nozzle re-design may provide greater flexibility for deliverables.

In an aspect, an embodiment of the invention includes to a method for transferring a solid body across a surface of a biological body. The method includes applying an electrical input to a controllable electromagnetic actuator. A mechanical force corresponding to the electrical input is produced with the electromagnetic actuator. The mechanical force is applied to a reservoir coupled at one end to a nozzle, the mechanical force producing a pressure within the reservoir. A magnitude of the pressure varies with the mechanical force and causes ejection of a fluid from the reservoir to drive the solid body into the biological body.

One or more of the following features may be included. Prior to the application of the mechanical force, the solid body may be disposed in the fluid in the reservoir, and the applied force produces a positive pressure ejecting at least a portion of the fluid and the solid body from the reservoir through the nozzle. The solid body may be disposed in a cartridge coupled to the nozzle prior to the application of the mechanical force. The applied mechanical force may produce a positive pressure to eject at least a portion of the fluid from the reservoir through the nozzle to drive the solid body through an orifice in the cartridge. The actuator may be bi-directional and the applied mechanical force may be applied in one of two directions. The solid body may be loaded into the reservoir by applying mechanical force in a first direction and thereafter driving the solid from the reservoir with applied force in a second direction opposite to the first direction.

In another aspect, embodiments of the invention include a method for delivering a substance to a target body. The method includes positioning a needle-free injector proximate to a surface of the target body, injecting the substance into the target body; and while injecting, moving the needle-free injector along the surface, thereby sweeping the surface.

One or more of the following features may be included. The needle-free injector may be positioned proximate and in contact with the target body. The needle-free injector may be moved along the surface in a plane. The substance may be injected to a plurality of depths below the surface. The injected substance may define a multi-layered structure including layers disposed at different depths beneath the surface. The target body may include tissue and/or the substance may include a solid body.

DETAILED DESCRIPTION

Figure 1:
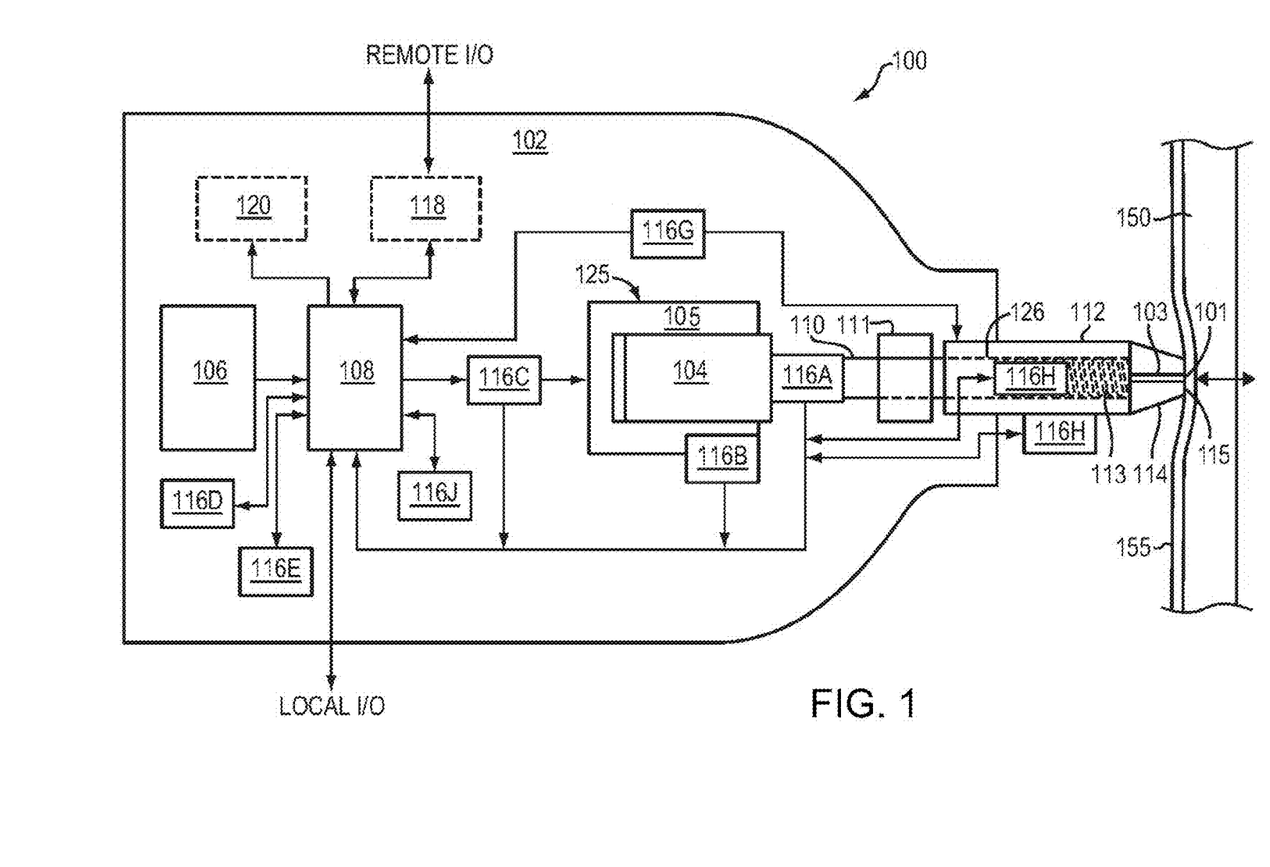
FIG. 1 is a schematic block diagram of an exemplary controllable, needle-free transdermal transfer device (i.e., jet injector), suitable for use with embodiments of the invention.

Referring to FIG. 1, an exemplary needle-free transdermal transport device 100, e.g., a needle-free injector, with servo-control capability suitable for use with embodiments of the invention to transfer a substance across the surface 155 of a biological body 150 may be configured as follows. Although one type of device is described in detail, the method of the invention may be practiced with a wide range of needle-free transdermal transport devices, and is not limited to the exemplary device.

The device 100 may be used to inject a liquid formulation of an active principle, for example, a drug, into a biological body such as an agriculture animal or human being. Alternatively or in addition, the same device 100 may be used to collect a sample from a biological body 150 by withdrawing the collected sample through the surface 155 of the body and into an external reservoir 113 that may be provided within the device 100.

The device 100 typically includes a nozzle 114 to convey the substance through the surface 155 of the biological body at the required speed and diameter to penetrate the surface 155 (e.g., skin) as required. The substance ejected from the nozzle 114 forms a jet, the force of the jet determining the depth of penetration. The nozzle 114 generally contains a flat surface, such as the head 115 that can be placed against the skin, and forms an orifice 101. The inner diameter of the orifice 101 controls the diameter of the transferred stream. Additionally, the length of an aperture, or tube 103, defining the orifice 101 also controls the transfer (e.g., injection) pressure.

The nozzle 114 may be coupled to a syringe 112 defining a reservoir 113 for temporarily storing the transferred substance. The syringe 112 may include a plunger or piston 126 having at least a distal end slidably disposed within the reservoir 113. Movement of the plunger 126 along the longitudinal axis of the syringe 112 in either direction creates a corresponding pressure within the reservoir 113. For example, a commercially-available needle-free syringe 112 can be attached to the device 100, such as a model reference no. 100100 syringe 112 available from Equidyne Systems Inc. of San Diego, Calif.

Beneficially, a pressure is selectively applied to the chamber 113 using a controllable actuator. Electromagnetic actuator 125 is configured to generate a high-pressure pulse having a rapid rise time (e.g., less than 1 millisecond). The actuator is dynamically controllable, allowing for adjustments to the pressure-versus-time during actuation.

The electromagnetic actuator 125 is configured to provide a linear force applied to the plunger 126 to achieve transdermal transfer of the substance. Transfer of the force can be accomplished with a force-transfer member 110, such as a rigid rod slidably coupled through a bearing 111.

The actuator 125 may include a stationary component, such as a magnet assembly 105, and a moveable component, such as coil assembly 104. A force produced within the coil assembly 104 may be applied to the plunger 126 directly or indirectly through the rod 110 to achieve transdermal transfer of the substance. Generally, the actuator 125, bearing 111 and syringe 112 are coupled to a frame or housing 102 that provides support and maintains fixed position of these elements during an actuation.

The device 100 may include a user interface 120 that provides a status of the device. The user interface may provide an indication that the device is ready for an actuation. For example, a light emitting diode (LED) coupled to a controller 108 may be enabled when sufficient conditions are satisfied for an injection. User interfaces 120 may include any suitable technology capable of conveying detailed information between a user and the device 100. The user interface 120 may also enable an operator to provide inputs as user selections for one or more parameters. Thus, a user may identify parameters related to dose, sample, and/or the biological body, such as age, weight, etc.

A power source 106 provides an electrical input to the coil assembly 104 of the actuator 125. An electrical current applied to the coil assembly 104 in the presence of a magnetic field provided by the magnet assembly 105 results in a generation of a mechanical force capable of moving the coil assembly 104 and exerting work on the plunger 126 of the syringe 112.

The controller 108 is electrically coupled between the power source 106 and the actuator 125. The controller 108 can selectively apply, suspend and otherwise adjust the electrical input signal provided by the power source 106 to the actuator 125. The controller 50 may be a simple switch operable by a local interface. For example, a button provided on the housing 102 may be manipulated by a user, selectively applying and removing an electrical input from the power source 106 to the actuator 125. The controller 108 may control elements, such as electrical circuits, that are adapted to selectively apply electrical power from the power source 106 to the actuator 125, the electrical input being shaped by the selected application.

The needle-free transdermal transport device 100 may include a remote interface 118. The remote interface 118 may be used to transmit information, such as the status of the device 100 or of a substance contained therein to a remote source. Alternatively or in addition, the remote interface 118 may be in electrical communication with the controller 108 and may be used to forward inputs received from a remote source to the controller 108 to affect control of the actuator 125.

The remote interface 118 can include a network interface, such as a local area network interface, a wide-area network interface, a modem or a wireless interface capable of interfacing with a remote device/user over a public-switched telephone network.

The controller 108 may receive inputs from one or more sensors adapted to sense a respective physical property. For example, the device 100 includes a transducer, such as a position sensor 116B to indicate location of an object's coordinates (e.g., the coil's position) with respect to a selected reference. Similarly, a displacement may be used to indicate movement from one position to another for a specific distance. Beneficially, the sensed parameter can be used as an indication of the plunger's position as an indication of dose. A proximity sensor may also be used to indicate a portion of the device, such as the coil, has reached a critical distance. This may be accomplished by sensing the position of the plunger 126, the force-transfer member 110, or the coil assembly 104 of the electromagnetic actuator 125. For example, an optical sensor such as an optical encoder can be used to count turns of the coil to determine the coil's position. Other types of sensors suitable for measuring position or displacement include inductive transducers, resistive sliding-contact transducers, photodiodes, and linear-variable-displacement-transformers (LVDT).

Other sensors, such as a force transducer 116A, may be used to sense the force applied to the plunger 126 by the actuator 125. As shown, a force transducer 116A can be positioned between the distal end of the coil assembly and the force transfer member 110, the transducer 116A sensing force applied by the actuator 125 onto the force transfer member 110. As this member 110 is rigid, the force is directly transferred to the plunger 126. The force tends to move the plunger 126 resulting in the generation of a corresponding pressure within the reservoir 113.

The actuator may be bi-directional, such that the mechanical force it generates may be applied in one of two directions. Accordingly, a positive force pushing the plunger 126 into the reservoir 113 creates a positive pressure tending to force a substance within the reservoir 113 out through the nozzle 114. A negative force pulling the plunger 126 proximally away from the nozzle 114 creates a negative pressure or vacuum tending to suck a substance from outside the device through the nozzle 114 into the reservoir 113. The substance may also be obtained from an ampoule, the negative pressure being used to pre-fill the reservoir 113 with the substance. Alternatively or in addition, the substance may come from the biological body representing a sampling of blood, tissue, and or other interstitial fluids. In some embodiments of the invention, as discussed below, a solid body may be loaded into the reservoir by applying mechanical force in a first direction and thereafter driving the solid from the reservoir with applied force in a second direction opposite to the first direction.

A pressure transducer (not shown) can also be provided to directly sense the pressure applied to a substance within the chamber.

An electrical sensor 116C may also be provided to sense an electrical input provided to the actuator 125. The electrical sensor 116C may sense one or more of coil voltage and coil current. Other sensors may include, for example, a gyrometer 116D, an accelerometer 116E, a strain gauge 116F, a temperature sensor 116G, an acoustic sensor or transducer 116H, and/or a barometric sensor 116J. The sensors 116A, 116B, 116C, 116D, 116E, 116F, 116G, 116H, and 116J (generally 116) are coupled to the controller 108 providing the controller 108 with the sensed properties. The controller 108 may use one or more of the sensed properties to control application of an electrical input from the power source 106 to the actuator 125, thereby controlling pressure generated within the syringe 112 to produce a desired transfer performance. For example, a position sensor can be used to servo-control the actuator 125 to pre-position the coil assembly 104 at a desired location and to stabilize the coil 104 once positioned, and conclude an actuation cycle. Thus, movement of the coil assembly 104 from a first position to a second position corresponds to transfer of a corresponding volume of substance. The controller can include a processor programmed to calculate the volume based on coil position give the physical size of the reservoir.

An actuation cycle generally corresponds to initiation of an electrical input to the actuator 125 to induce transfer of a substance and conclusion of the electrical input to halt transfer of the substance. A servo-control capability combined with the dynamically controllable electromagnetic actuator 125 enables adjustment of the pressure during the course of an actuation cycle. One or more of the sensors 116 can be used to further control the actuation cycle during the course of the transfer, or cycle. Alternatively or in addition, one or more of local and remote interfaces can also be used to further affect control of the actuation cycle.

The controller 108 may be coupled with one or more other sensors (not shown) that detect respective physical properties of the biological surface. This information may be used to servo-control the actuator 125 to tailor the injection pressure, and, therefore, the depth of penetration of drug into the skin for a particular application. Moreover, the injection pressure may be varied over time.

Figure 2A:
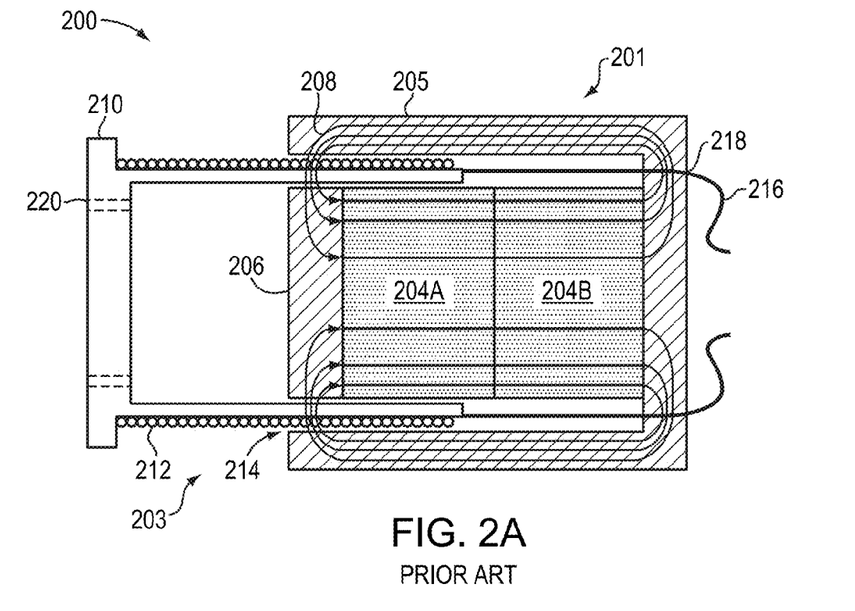
FIGS. 2A and 2B are cross-sectional diagrams of a controllable electromagnetic actuator usable with the device of FIG. 1, shown in extended and retracted configurations, respectively.

A cross-sectional diagram of an electromagnetic impulse actuator 200 is shown in FIG. 2A. The actuator 200 includes a magnet assembly 205 defining an annular slotted cavity 214 and a coil assembly 203 slidably disposed therein. The stroke of the coil 203 may be controlled by the lengths of the coil and magnet assembly.

The magnet assembly 205 includes a column of magnets 204A, 204B disposed along a central axis. The column of magnets may be created by stacking one or more magnetic devices, such as permanent magnets. A suitable category of strong, high-density magnets are rare-earth magnets, also known as Neodymium-Iron-Boron magnets (e.g., $Nd_2Fe_{14}B$), such as N50 magnets. The magnetic field produced by the magnets generally follows field lines 208.

The magnets 204A, 204B are attached at one end of a right-circular cylindrical shell 201 defining a hollowed axial cavity and closed at one end. An annular slot remains being formed between the magnets 204A, 204B and the interior walls of the case and accessible from the other end of the shell 201. An exemplary shell 201 is formed with an outside diameter of about 40 mm and an inside diameter of about 31.6 mm, resulting in a wall thickness of about 4.2 mm. The magnets 204A, 204B may be cylindrical, having a diameter of about 25.4 mm.

The shell 201 is preferably formed from a material adapted to promote containment of the magnetic fields produced by the magnets 204A, 204B. For example, the shell 201 may be formed from a ferromagnetic material or a ferrite. One such ferromagnetic material includes an alloy referred to as carbon steel (e.g., American Iron and Steel Institute (AISI) 1026 carbon steel). An end cap 206 is also provided of similar ferromagnetic material being attached to the other end of the magnets 204A, 204B. Placement of the end cap 206 acts to contain the magnetic field therein and promoting a radially-directed magnetic field between the annular gap formed between the end cap 206 and the outer walls of the shell 201. The end cap is generally thicker than the shell walls to promote containment of the magnetic fields as they loop into the end of the top magnet 204A. For the exemplary shell 201 described above, the end cap 206 has an axial thickness of about 8 mm.

The coil assembly 203 includes a coil 212 formed from a conducting material, such as copper wire wound about a bobbin 210. The bobbin 210 can be cylindrical and defines an axial cavity sized to fit together with the coil 212 within the annular cavity 214. The bobbin 210 may be substantially closed at the end juxtaposed to the annular cavity 214. The closed end forms a force-bearing surface adapted to push against a plunger 214 or force-bearing rod 210.

A strong, yet light-weight coil assembly 203 is preferred for applications requiring a rapid generation of substantial force, such as needle-free transfers. Preferably, the bobbin 210 is formed from a strong, yet light-weight readily machinable material, for example poly-acetal resins which are particularly well-suited to high temperature applications. The bobbin 210 is thin-walled to fit within the annular slot. A thin-walled bobbin 210 allows for a narrower annular slot 214 thereby promoting a greater magnetic field intensity across the gap.

The bobbin 210 may have an outside diameter of about 27 mm, an internal diameter of about 26 mm, and an axial length of about 46 mm. The coil 212 consists of six layers of 28 gauge copper wire wound onto the bobbin 210 at a rate of about 115 windings per coil length (about 35 mm) resulting in about 700 turns total. Using the N50 magnets with the 1026 carbon steel, the end cap 206 contains between about 0.63 and 0.55 Tesla (the value reducing outwardly along a radius measured from the center of the end cap 206).

Thus, a current flowing through the coil 212 is positioned at right angles to the magnetic field 208 produced between the end cap 206 and the shell 201 wall. This results in the generation of a force on the coil directed along the longitudinal axis, the direction of the force depending upon the directional flow of the current. For the above exemplary device, an electrical input, or drive voltage of about 100 volts is applied across the coil for a duration of about 1 millisecond representing the pierce phase of an actuation cycle. A lesser electrical input of about 2-5 volts is applied for the transfer phase.

Generally, the coil 212 receives the electrical input signal through two electrical leads 216. The shell 201 includes one or more apertures 218 through which the leads 216 are routed to the power source 106 (FIG. 1). The closed end of the shell 201 may contain one or more additional apertures through which air may be transferred during movement of the coil. Without such apertures and given the relative tight tolerances of the gap between the coil 212 and the annular slot 214, a pressure would build up to oppose movement of the coil. Alternatively or in addition, the bobbin 210 may also have one or more apertures 220 to further inhibit the build up of damping pressures during actuation.

Figure 2B:
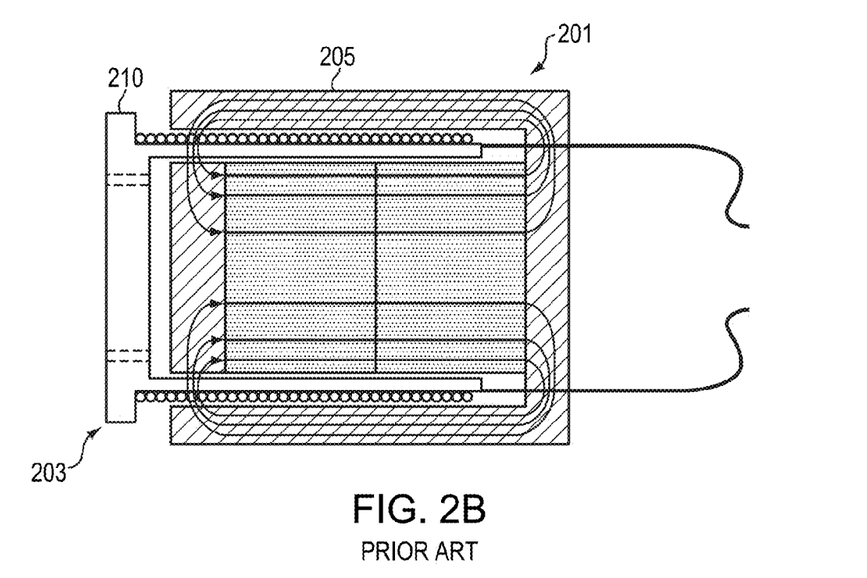

FIG. 2A shows the coil assembly 203 after or during an injection phase in which the coil is forced out of the shell 201 thereby advancing the front plate 215. FIG. 2B shows the coil assembly 203 retracted within the shell 201 after a sampling phase in which the coil assembly 203 is drawn into the shell 201.

The conductive coil may be configured to carry a relatively high-amplitude electrical current to produce a substantial force resulting in the generation of a substantial pressure. The coil also provides a relatively low inductance, e.g., less than 100 millihenries to support high-frequency operation. One way to provide high-current capacity with the low inductance is using a coil formed by a large-diameter conductor that is configured with a low number of turns (e.g., 1 to 3 turns).

The result is a pressure actuator capable of generating a high-pressure pulse with a rapid rise time. Additionally, operation of the actuator is both controllable and highly predictable given the physical properties of the actuator and the input electrical current. Still further, the actuator is reversible providing forces in opposing directions based on the direction of current flow within the coil.

Figure 3A:
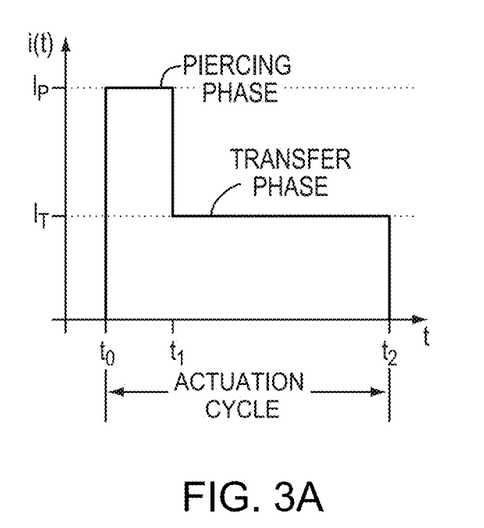
FIG. 3A is a graph depicting a current-versus-time profile of an exemplary electrical input to the controllable electromagnetic actuator of FIGS. 2A-2B.

Additionally, the controllability allows for a tailored injection profile that can include a rapid high-pressure pulse to breach the outer layers of skin, followed by a lower-pressure, prolonged pulse to deliver the formulation. Referring to FIG. 3A, an exemplary time varying electrical input is shown. The curve represents variation in an electrical current applied to the coil assembly 104 of the actuator 125. At a first instant of time $t_0$ an electrical current is applied to the coil 104. The current rises from a rest value (e.g., zero amps) to a maximum value $I_P$ remaining at this maximum for a selectable duration and then transitioning to a different current value $I_T$ at a later time $t_1$. The current amplitude may remain substantially at this value, or continue to vary with time until a later time $t_2$, at which the current returns to a rest value.

The entire period of time defined between times $t_2$ and $t_0$ can be referred to as an actuation period, or actuation cycle. For a current input having a shape similar to that just described, the period defined between times $t_1$ and $t_0$ can be referred to as a piercing phase. As the name suggests, the high current value $I_p$ induces a corresponding high pressure that can be used to pierce the surface of a biological body without using a needle or lance. The remainder of the actuation cycle defined between times $t_2$ and $t_1$ can be referred to as a transfer phase. As this name suggests, the relatively lower current value $I_T$ induces a lesser pressure that can be used to transfer a substance from the reservoir 113 (FIG. 1) to the biological body through the perforation in the surface created during the piercing phase.

Figure 3B:
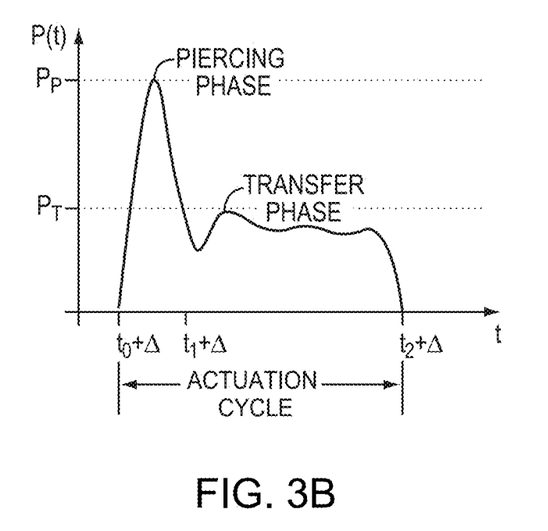
FIG. 3B is a graph depicting a pressure-versus-time profile of an exemplary pressure generated within a reservoir used in the transfer of a substance, the pressure being generated by the controllable electromagnetic actuator responsive to the electrical input of FIG. 3A.

An exemplary plot of a pressure induced within the reservoir 113 (FIG. 1) in response to the electrical input is illustrated in FIG. 3B. As shown, the pressure rises from an initial rest value to a relative maximum value, $P_p$, at a time $t_0$, perhaps with a slight delay Δ resulting from the transfer characteristics of the electrical coil. This pressure value can be used to create a jet as described above in relation to FIG. 1. As the current is reduced during the transfer phase, the pressure similarly reduces to a lesser value $P_T$ determined to achieve a desired transfer of the substance. The transfer phase continues until a desired volume of the substance is transferred, then the pressure is removed concluding the actuation cycle.

A servo-controlled injector includes a specially-designed electromagnetic pressure actuator configured in combination with a servo controller to generate an injection pressure responsive in real-time to one or more physical properties (e.g., pressure, position, volume, etc.). In some embodiments, the servo-controlled injector is a needle-free device. The electromagnetic pressure actuator generates a high-pressure pulse having a rapid rise time (e.g., less than 1 millisecond) for injecting a formulation beneath the skin. With such a rapid rise time, an entire transfer can be completed in less than about 10 milliseconds. The pressure provided by the actuator can be varied during the actuation of a single injection to achieve a desired result. For example, a first high-pressure is initially provided to the formulation to penetrate the outer surface layer of an animal's skin. Once the skin is penetrated, the pressure is reduced to a second, lower pressure for the remainder of the injection. The servo-controller can be used to determine when the skin is penetrated by sensing a change in pressure within the chamber and to adjust the injection pressure accordingly.

A servo-controller 108 receives input signals from the one or more sensors 116 and generates an output signal according to a predetermined relationship. The servo-controller output can be used to control the pressure by controlling the amplitude of electrical current driving the controllable actuator.

Real-time control can be accomplished by the servo controller 108 repeatedly receiving inputs from the sensors 116, processing the inputs according to the predetermined relationship and generating corresponding outputs. In order to adjust the injection pressure during the course of an injection, the entire sense-control process is preferably performed numerous times during the period of the injection. For example, a servo-controller 108 can include a high-speed microprocessor capable of processing signals received from the sensors and rapidly providing corresponding output signals at a rate of 100 kHz (i.e., every 10 microseconds). Such rapid response times provide hundreds of opportunities to adjust pressure during the course of a single 5 to 10 millisecond injection.

Figure 4:
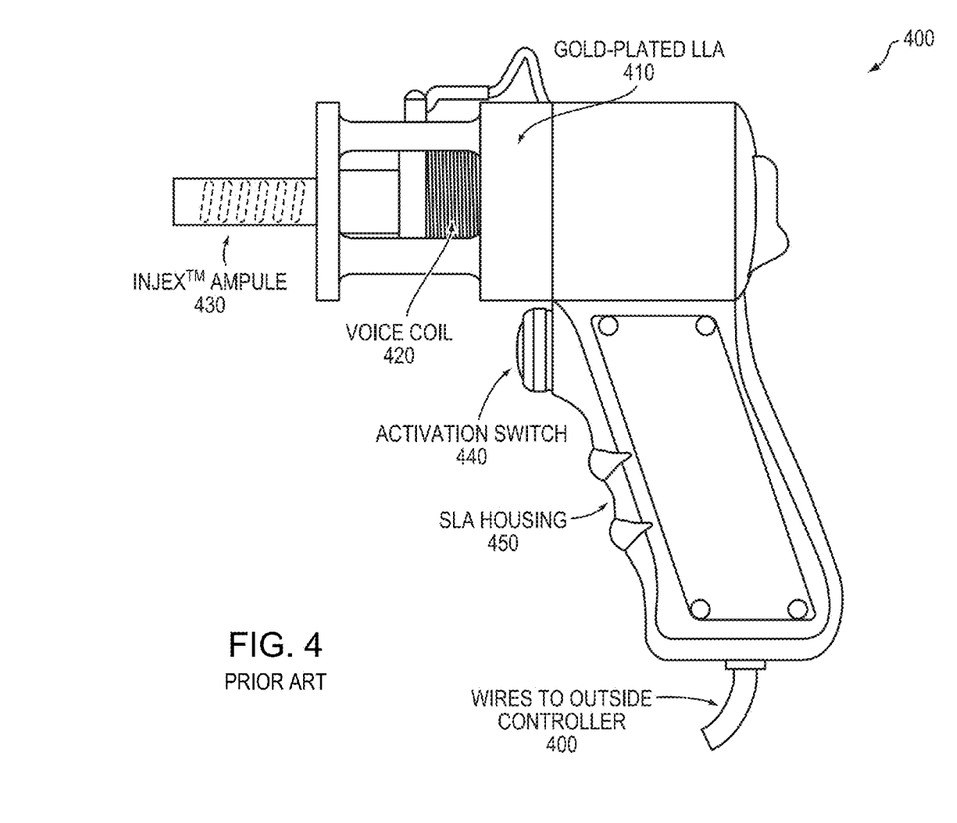
FIG. 4 is a photograph of a handheld servo-controlled jet injector that may be used in the present invention.

Referring to FIG. 4, a servo-controlled jet injector suitable for use with embodiments of the invention includes a handheld injector 400, a real-time controller (not shown), and a linear power amplifier The hand held injector 400 comprises a voice coil 420 that slides freely along a steel extrusion as it moves in the motor 410, an ampoule, such as commercially available disposable Injex™ 30 ampoule 430 (0.3 mL; part #100100 available from Injex-Equidyne Systems, Inc., based in Fullerton, Calif.), a push button activation switch 440, housing 450 that surrounds the interior components of the injector, and wires 460 that connect to a controller.

Figure 5:
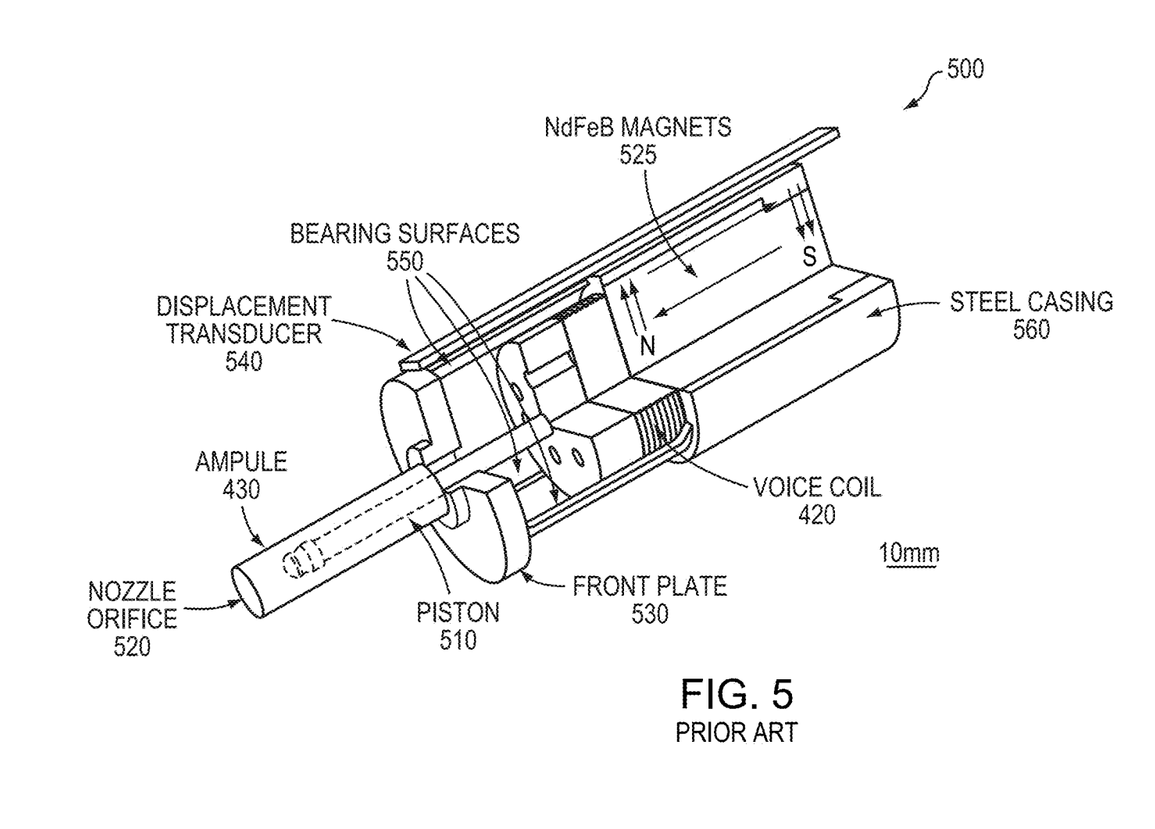
FIG. 5 is a cut-away schematic view of one embodiment of a controllable electromagnetic actuator suitable for use with the device of FIG. 4.

In the cut-away shown in FIG. 5, the Injex™ 30 ampoule 430 is screwed into a front plate 535 of the jet injector and the piston 510 is threaded into the front of the moving coil 420. The choice of ampoule may be based on availability, relatively low cost, proven performance, and ease with which it may be adapted for inclusion into the injection device. The internal diameter of the ampoule may taper at the tip to form a nozzle orifice 520 having a diameter of, e.g., 220±5 μm. In the illustrated embodiment, a delivery volume of 300 μL is realized with a 30 mm stroke.

The custom-designed linear Lorentz-force motor consists of 582 turns of 360 μm diameter enameled copper wire wound six layers deep on a custom-designed, thin-walled former. The former may be machined from polyetherimide stock; the material choice that permits minimization of the moving mass (~50 g) and avoids the drag incurred by induction of eddy currents in a conducting former. Current applied to the copper wire creates an axial Lorentz force of up to 200 N with a force constant of 10.8±0.5 N/A. The total DC resistance of the coil may be approximately 11.3 Ω.

The voice coil 420 slides freely and smoothly on the bearing surfaces 550 and inside a 1026 carbon-steel extrusion casing 560 that also forms the magnetic circuit. The latter includes two 0.4 MN/m$^2$ (50 MGOe) NdFeB magnets 525 inserted into the casing. The magnetic flux density in the field gap may be approximately 0.6 Tesla.

Plastic-laminated, flexible copper ribbons may form the electrical connections to the coil. A 10 kΩ linear potentiometer (i.e., displacement transducer) 540 with >1 kHz bandwidth may be mounted to the linear guide system monitors the position of the coil. The position sensor is coupled to the coil via a movable pin that is mounted on the leading edge of the former. The system is powered by a 4 kW Techron amplifier, controlled by a PC-based data acquisition and control system running in National Instruments Labview™ 8.5, which allows the testing of a variety of waveforms and concomitant evaluation of both the current and displacement.

High-speed position monitoring and servo-control of coil position may be achieved using a compact reconfigurable system comprising a real-time controller (cRIO-9004, National Instruments, Austin, Tex.) embedded in a reconfigurable field-programmable gate-array (FPGA) chassis (cRIO-9104). The controller may execute a LabVIEW 8.5 Real-Time "host" application that interacts with the FPGA circuitry, perform high-level injection trajectory planning, interpret user commands, and provide real-time and post-injection feedback. The user interface of the host application may be broadcast by a web-server running on the controller, and operated from a web-browser on a networked laptop computer.

Figure 6:
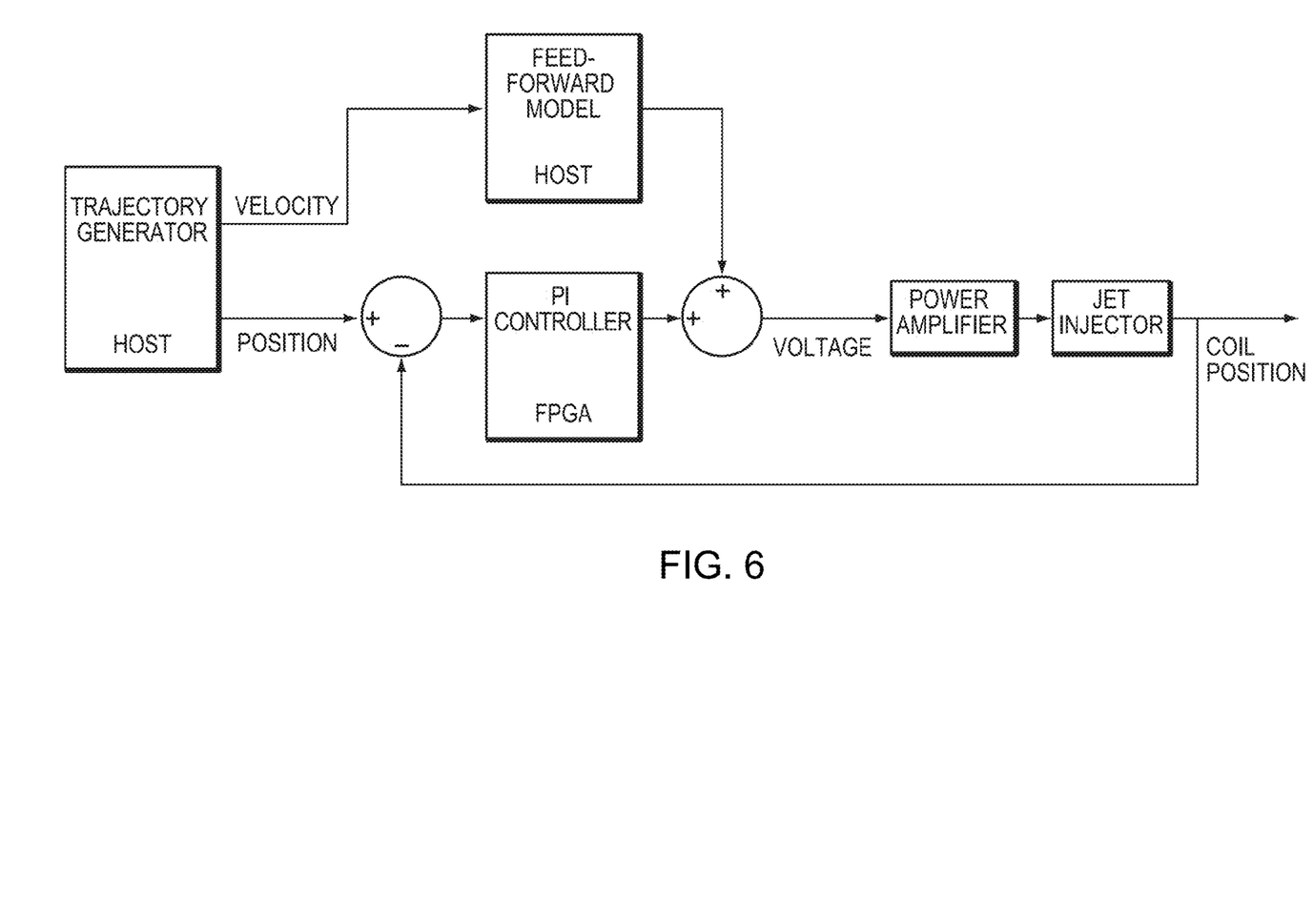
FIG. 6 is a block diagram of one embodiment of the control system architecture usable with the device of FIG. 4.

The position-based jet-injector control algorithm has two components: (i) a velocity-driven feed-forward (FF) model that predicts the voltage required to achieve a given jet-speed, and (ii) a linear proportional-integral (PI) displacement feedback controller to counteract noise and disturbances to the injector system, as depicted in FIG. 6. Both components are active when the coil is in motion; FF dominates during injections while the feedback dominates during refilling and holding and ensures that the correct volume of fluid is delivered.

Injection waveforms (or trajectories) are generated with two distinct phases of delivery: a brief high-speed phase followed by a second lower speed phase of variable duration. The first phase accelerates the coil to the desired jet velocity ($V_{jet}$) required for penetration where it is maintained for a pre-determined period of time ($T_{jet}$) after which the coil is gently decelerated to a lower follow-through velocity ($V_{ft}$). This velocity is maintained until the coil position approaches the displacement at which the desired injection volume (V) is realized. Feedback of jet speed is implicit from position feedback, with the derivative or slope of the coil vs. time plot representing velocity. The integral of the position vs. time plot yields the volume being delivered.

In one embodiment of the invention, the jet injection device of FIG. 1 may be used to inject a solid body, such as bare or functionalized polymer wires or metal wires across a surface of a biological body, e.g., into tissue (e.g., brain) or some other material for use as recording electrodes. The dimensions and depth of injection may vary depending on use.

In an exemplary embodiment, wires (polymer or metal) for neural recording may be tethered at one end to the piston tip of a fluid-filled ampoule and injected into tissue such that the tip of each wire protrudes from the tissue surface, allowing the wires to be integrated into a microelectrode array assembly for recording. Such wires may range in diameter from 10 μm to 200 μm and may have lengths of 200 μm to 15 mm.

Figure 7:
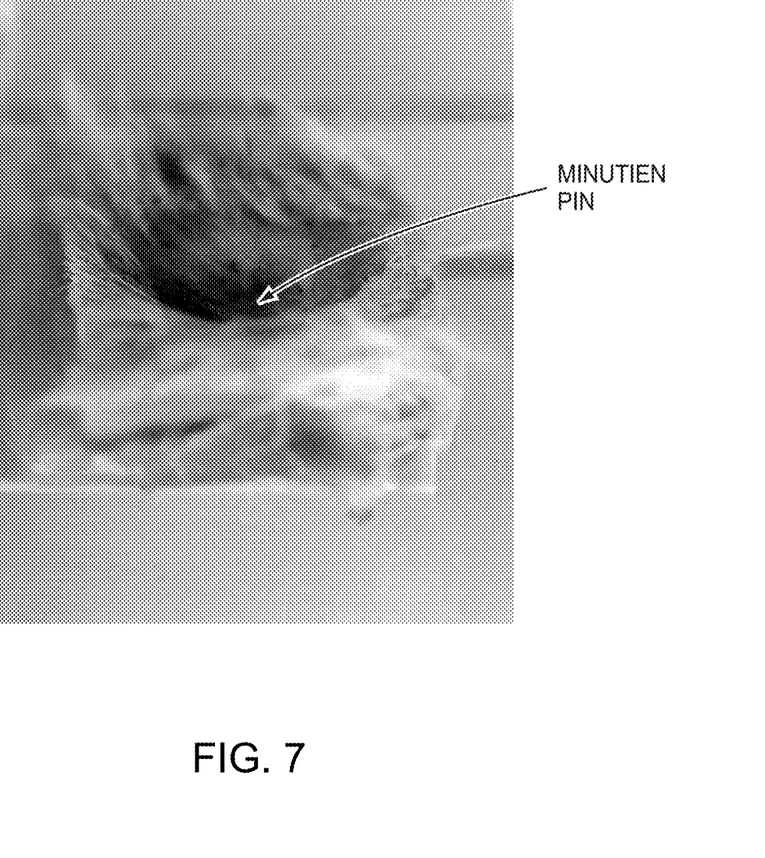
FIG. 7 illustrates delivery of minutien pins using a hand-held servo-controlled jet injector as shown in FIG. 4.

Referring to FIG. 7, a photograph shows delivery of 0.1 mm×11 mm metal pins or wires (i.e., minutien pins) to post mortem rat skin using a servo-controlled linear Lorentz-force actuator as shown in FIG. 4. Individual minutien pins were seated in the nozzle of fluid filled ampoules, which were then apposed to tissue and the pins ejected. Pins were shown to completely penetrate rat skin when delivered by ejection of 50 μL of fluid at a jet speed of 150 m/s. $T_{jet}$ and $V_{ft}$ were constant at 5 ms and 50 m/s respectively.

In another embodiment of the invention, the device of FIG. 1 may be used to inject particles <100 μm in diameter (e.g., nanoparticles and microparticles) suspended in fluid into tissue, tissue analogues, etc. The particles may be functionalized. The suspended particles may be loaded into the device by utilizing the bidirectional nature of the motor. Microparticles having diameters >100 μm may be ejected with some modification of the nozzle orifice; for example the nozzle diameter may be enlarged to accommodate delivery of larger particles, nozzle length may be reduced to reduce fluid pressure drop, or the taper of the nozzle may be changed.

Figure 8A:
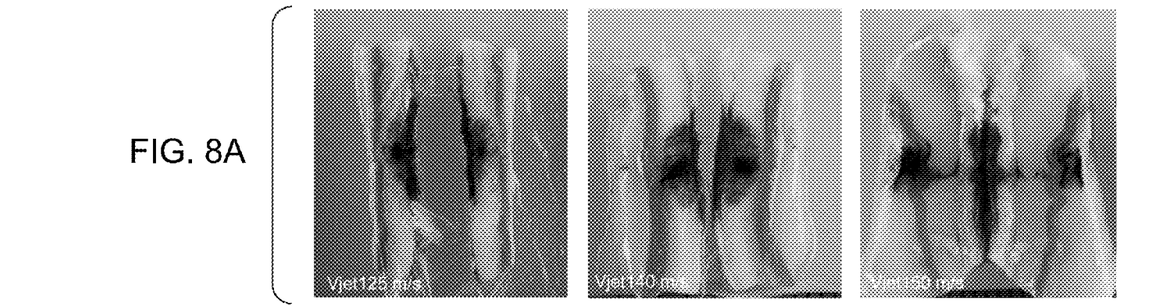
FIGS. 8A, 8B, and 8C illustrate delivery of a constant volume of 6 μm polystyrene beads in water to variable depths in post mortem rat skin using variable jet velocities ($V_{jet}$) with constant time at jet velocity ($T_{jet}$) and follow-through velocity ($V_{ft}$)

Referring to FIG. 8A, representative photographs showing delivery of 6 μm spherical polystyrene beads in water to post mortem rat skin using the injection device of FIG. 4. Beads were delivered using $V_{jets}$ of 100, 125, 140, and 150 m/s with a constant $T_{jet}$ of 5 ms and $V_{ft}$ of 50 m/s; a $V_{jet}$ of 100 m/s failed to penetrate the tissue. Post injection, the tissue was cut down the midline of the injection site, splayed injection side up, and photographed.

Figure 8B:
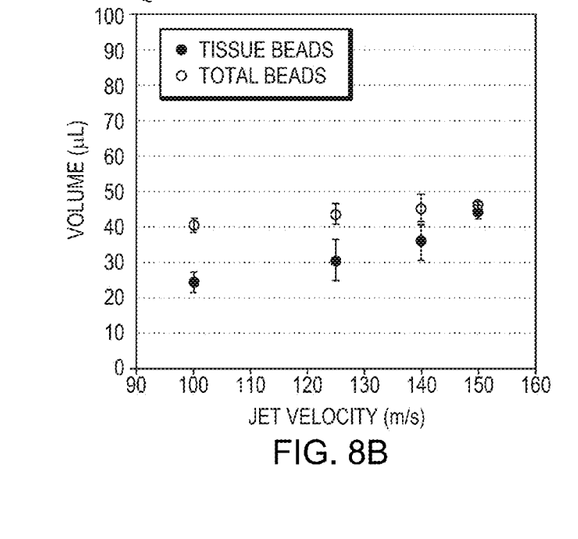

The volume of beads in water injected into the tissue may be calculated as the difference in tissue weight, pre- to post-injection after subtracting the weight of any fluid remaining on the surface of the tissue post injection; the latter being blotted to pre-weighed filter paper and re-weighed. FIG. 8B is a graph depicting the total volume of beads in water delivered and the volume of beads in water delivered to the tissue as a function of jet velocity. Total volume delivered was >80% while volume delivered specifically to the tissue varied with jet velocity. Extremes at 100 m/s and 150 m/s represent insufficient pressure to penetrate the tissue or complete penetration of the tissue respectively.

Figure 8C:
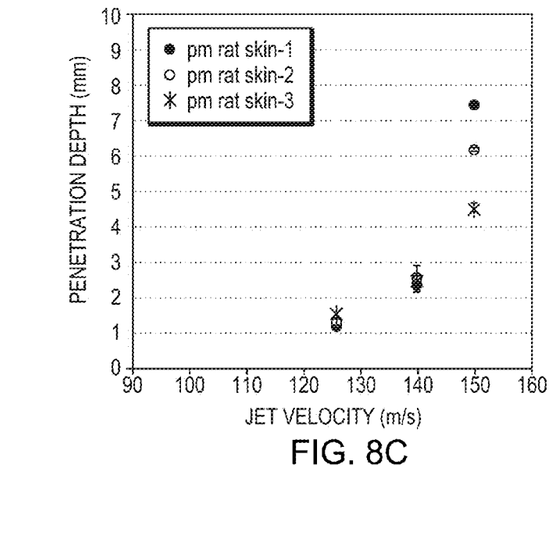

FIG. 8C is a graph showing that penetration depth increases with increasing jet velocity, as depicted in FIG. 8A. The variation in depth observed at 150 m/s is independent of the velocity. Rather it reflects the variation in the total depth of the tissue as this velocity repeatably completely penetrated the tissue sample.

Figure 9:
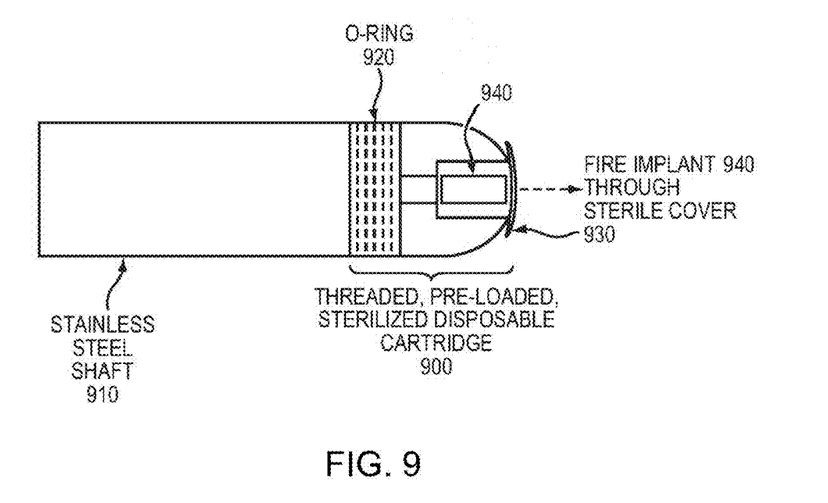
FIG. 9 is a schematic drawing of an embodiment of a cartridge design.

Referring to FIG. 9, in another embodiment of the invention, the ampoule and/or nozzle of the device illustrated in FIG. 1 may be modified to hold a pre-loaded, single use cartridge 900. The cartridge may be made out of a clear plastic, for example polycarbonate with a nozzle geometry capable of holding a capsule or implant 940 taking the shape of, for example a sphere, rod, etc. Contiguous with the capsule receptacle is a through hole passage that lines up with a similar passage in the stainless steel shaft 910 holding the piston. The distal end of the nozzle may be threaded, allowing it to be seated onto the end of a stainless steel shaft containing a plunger that may be loaded with fluid. Optionally, an O-ring 920 may be disposed proximate the threads. Both the stainless steel shaft and the plunger may be made from materials that can be sterilized. A sterile cover 930 may be placed over an end of the ampoule. Actuation results in the plunger forcing the fluid through the capsule orifice, causing the implant 940 to be ejected from the cartridge through the sterile cover and into the target tissue.

In some embodiments, the actuator may be used to propel shards of glass-forming sugars such as trehalose and sucrose that contain drug into tissue. Sugars are often used as excipients because their transition temperature correlates with the storage temperature of the product.

Another embodiment relates to use of the servo-controlled jet injector platform to deliver a series of incremental volumes of fluid containing one or more solid particulates to a target body, such as an agriculture animal, pet, or human being. Ejection of the fluid drives the particulates into the target body to pre-determined depths and may result in the formation of, for example self-assembling scaffolds or multi-layered structures. Assembly may be due to:
- interaction between independently delivered particulates;
- interaction based on a change of state of the particulates and/or fluid once injected;
- interaction due to stacking of the particulates relative to one another as a result of delivery to different depths; and/or
- interaction due to stacking of particulates and fluid based on both delivery depth and a change of state once injected.

Figure 10:
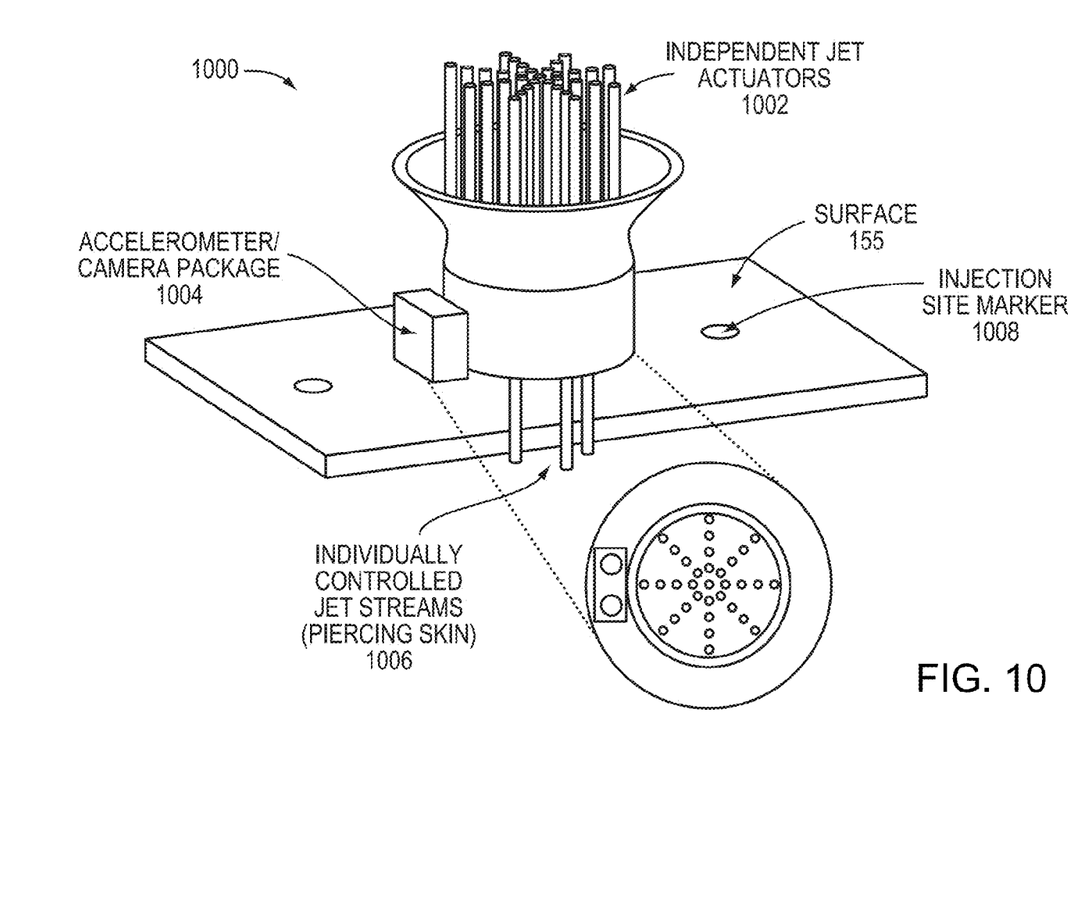
FIG. 10 is a perspective diagram showing surface treatment using a servo-controlled multi-shot needle-free jet injection device.

Referring to FIG. 10, injection may be accomplished by positioning a needle-free injector 1000 including a number of independent jet actuators 1002 and having an ampoule attached thereto, e.g., needle-free transdermal transport device 100 or hand-held injector 400, proximate a surface 155 of the target body, e.g., tissue of a biological body, injecting a substance into the target body, and, while injecting, moving the needle-free injector along the surface, thereby sweeping the surface. The surface may be swept using one or more actuators. The sweeping motion of the device may be servo-controlled using an accelerometer 1004, e.g., disposed in an accelerometer/camera package, while the orientation of the device during the sweeping motion may be controlled using a 3-axis gyrometer. The needle-free injector may inject, e.g., individually controlled jet streams 1006 along a number of injection sites that may be marked by markers 1008 disposed in the swept area, i.e., in the treated surface region 1008. During injection the needle-free injector may be in contact with the target body. The needle-free injector may be moved along the surface in a plane. The substance may be injected to a plurality of depths below the surface. The injected substance may define a multi-layered structure including layers disposed at different depths beneath the surface. The substance may include or consist essentially of a solid body.

One of skill in the art will recognize that a number of needle-free injectors, in addition to the exemplary needle-free transdermal transport device 100 and hand-held injector 400, may be used in methods in accordance with embodiments of the invention. Moreover, those skilled in the art will readily appreciate that all parameters listed herein are meant to be exemplary and actual parameters depend upon the specific application for which the methods and materials of the present invention are used. It is, therefore, to be understood that the foregoing embodiments are presented by way of example only and that, within the scope of the appended claims and equivalents thereto, the invention may be practiced otherwise than as specifically described. Various materials, geometries, sizes, and interrelationships of elements may be practiced in various combinations and permutations, and all such variants and equivalents are to be considered part of the invention.

What is claimed is:

1. A method for transferring a solid body across a surface of a biological body, the method comprising the steps of:
   disposing the solid body in a cartridge coupled to a nozzle;
   applying an electrical input to a controllable electromagnetic actuator;
   producing with the electromagnetic actuator a mechanical force corresponding to the electrical input; and
   applying the mechanical force to a reservoir coupled at one end to the nozzle, the mechanical force producing a pressure within the reservoir, a magnitude of the pressure varying with the mechanical force and causing needle-free ejection of a fluid from the reservoir through the nozzle into the cartridge to drive the solid body from the cartridge and into the biological body, the cartridge being separate from the reservoir.

2. The method of claim 1, wherein the actuator is bi-directional and the applied mechanical force is applied in one of two directions.

3. The method of claim 1, wherein the solid body includes a drug-filled capsule.

4. The method of claim 1, wherein the solid body includes an implant.

5. The method of claim 1, wherein the solid body includes an RFID tag.

6. The method of claim 1, wherein the solid body includes self-assembling scaffolds.

7. The method of claim 1, wherein the solid body includes a wire.

8. The method of claim 1, wherein the solid body includes a sensor.

9. The method of claim 1, wherein the solid body includes a microparticle having a diameter greater than 100 micrometers.

10. A needle-free transport device for transferring a solid body across a surface of a biological body comprising:
a reservoir for storing a fluid;
a nozzle coupled to the reservoir;
a cartridge coupled to the nozzle and containing a solid body, the cartridge being separate from the reservoir; and
a controllable electromagnetic actuator in communication with the reservoir, the actuator receiving an electrical input and generating a mechanical force corresponding to the electrical input, the mechanical force producing a pressure within the reservoir, a magnitude of the pressure varying with the mechanical force and causing needle-free ejection of the fluid from the reservoir through the nozzle into the cartridge to drive the solid body from the cartridge and into the biological body.

11. The device of claim 10, wherein the cartridge has an orifice, the solid body being driven from the cartridge through the orifice.

12. The device of claim 11, wherein the cartridge comprises a sterile cover sealing the orifice, the solid body being driven through the cover.

13. The method of claim 1, wherein the cartridge has an orifice, the solid body being driven from the cartridge through the orifice.

14. The method of claim 13, wherein the cartridge comprises a sterile cover sealing the orifice, the solid body being driven through the cover.

15. The device of claim 10, wherein the actuator is bi-directional and the mechanical force is applied to the reservoir in one of two directions.

16. The device of claim 10, wherein the solid body includes a drug-filled capsule.

17. The device of claim 10, wherein the solid body includes an implant.

18. The device of claim 10, wherein the solid body includes an RFID tag.

19. The device of claim 10, wherein the solid body includes self-assembling scaffolds.

20. The device of claim 10, wherein the solid body includes a wire.

21. The device of claim 10, wherein the solid body includes a sensor.

22. The device of claim 10, wherein the solid body includes a microparticle having a diameter greater than 100 micrometers.

* * * * *